United States Patent [19]

Berman

[11] 4,411,014

[45] Oct. 18, 1983

[54] TOOL FOR INSPECTING THE UPPER END OF A STRING OF CASING SET IN THE BOTTOM OF A BODY OF WATER

[75] Inventor: Mark Y. Berman, Tulsa, Okla.

[73] Assignee: Standard Oil Company, Chicago, Ill.

[21] Appl. No.: 277,580

[22] Filed: Jun. 26, 1981

[51] Int. Cl.³ .............................................. G01N 23/18
[52] U.S. Cl. ...................................... 378/59; 378/058
[58] Field of Search .................. 378/58, 59, 182, 184, 378/177, 62

[56] References Cited

U.S. PATENT DOCUMENTS 2,390,211 12/1945 Forssell .................................. 378/59
3,214,586 10/1965 Graham .................................. 378/58

Primary Examiner—Alfred E. Smith
Assistant Examiner—T. N. Grigsby
Attorney, Agent, or Firm—John D. Gassett

[57] ABSTRACT

An inspection tool for detecting any flaws or defects in the upper end of a string of casing set in the bottom of a body of water. The tool has a cylindrical housing carrying a radiographic-sensitive film which fits over the open end of the string of casing and a radiographic source supported in the axis of the cylindrical housing. Means are provided for raising and lowering the tool.

3 Claims, 3 Drawing Figures

TOOL FOR INSPECTING THE UPPER END OF A STRING OF CASING SET IN THE BOTTOM OF A BODY OF WATER

BACKGROUND OF THE INVENTION

This invention relates to the inspection of the upper end of casing set in the bottom of a body of water to which riser pipes can be connected which extend to a floating structure.

In recent years there has been attention directed toward many different kinds of floating structures. One system receiving attention for mooring is the so-called Vertically Moored Platform (VMP). A Vertically Moored Platform can be described as a floating marine structure for drilling wells and/or producing hydrocarbons from an underwater formation and anchored by essentially parallel, vertical, and elongated members such as riser pipe. Riser pipes are usually considered to be heavywalled, 18-inch steel pipe. In the preferred form of a Vertically Moored Platform, the riser pipes are without slip joints and provide the only anchoring means for the Vertically Moored Platform. Such a platform is described in several patents, including U.S. Pat. No. 3,648,638, issued Mar. 14, 1972, Kenneth A. Blenkarn, inventor.

In these instances of the Vertically Moored Platform, a plurality of casing is set in a selected pattern in the bottom of the body of water so as to resist any upward force. The upper end of these set casings are provided with connectors which mate with connectors on the lower end of riser pipes which are supported by and lowered from the floating structure. Once the connection is made between the riser pipes and the said casing, the structure is anchored.

Perhaps the closest known prior art is the well-known systems of using x-ray to inspect welds in pipelines.

BRIEF DESCRIPTION OF THE INVENTION

This concerns an inspection of a submerged upper end of a casing set in the bottom of a body of water which has a connector to which the lower end of a riser pipe having a suitable mating connector can be lowered to and attached. This inspection tool includes a cylindrical housing having one end open and larger than the casing, a radiographic source carried within the housing, radiographic film carried on the interior of said housing, and means to energize the radiographic source from a location remote from said inspection tool.

The inspection tool is normally attached to the lower end of a string of drill pipe and is lowered until the inspection tool surrounds the connector on the said casing string. The radiographic source is then activated to expose the radiographic film so that any defects in the connector will be shown on the film when developed.

DRAWINGS

DETAILED DESCRIPTION

Figure 1:
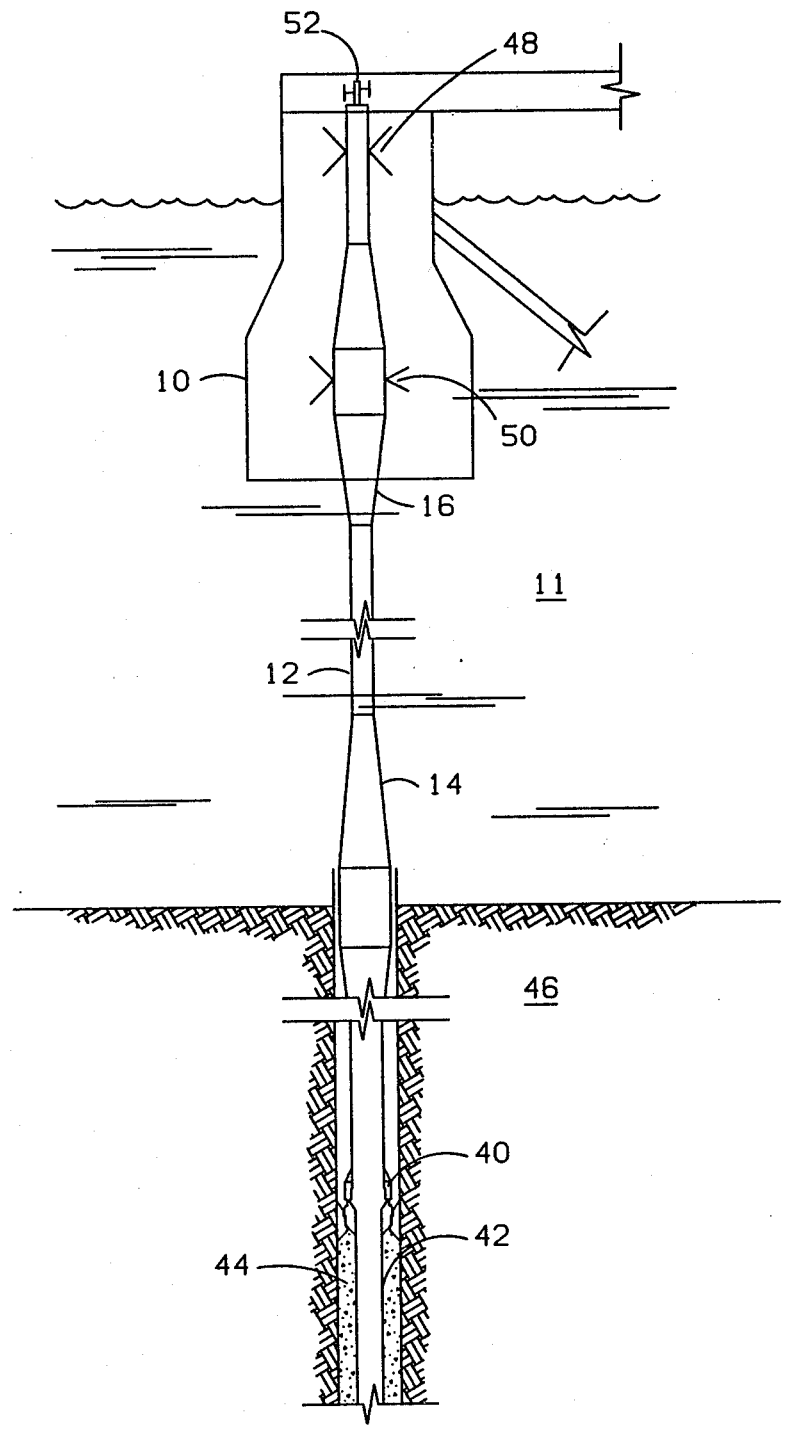
FIG. 1 illustrates one leg of one of the buoyant structures of a Vertically Moored Platform.

Attention is first directed to FIG. 1 which shows a riser pipe 12 connecting a leg 10 of a floating vessel or structure not shown with a set casing 34. This system is shown in U.S. Pat. No. 4,062,313, issued Dec. 13, 1977, for installation of Vertically Moored Platforms. This invention is not limited to any particular form of floating structure or particular riser pipe configuration, and FIG. 1 is shown to illustrate what is believed to be a particularly important application of this invention. Shown is a buoyant leg 10 floating on a body of water 11 connected by riser pipe 12 through various connectives to a conductor casing 42 cemented in a hole in bottom 46. There are typically four buoyant members 10. Although only one riser pipe 12 is shown, there would normally be eight for each buoyant member 10. Included in the riser pipe system are an upper terminator section 16 and a lower terminator section 14. The nature of these terminators and connectors are shown clearly in said U.S. Pat. No. 4,062,313. The lower end of riser terminator 14 is connected through a connector 40 to a conductor 42, which is set in the hole and secured there by cement 44. Conductor 42 is typically a 20-inch string of steel pipe or casing which is set in the bottom 46 below the body of water 11. Vertical bearing 48 and horizontal bearings 50 are indicated and a wellhead 52 is shown at the top of an upper riser terminator 16. Vertical bearings are shown in U.S. Pat. No. 4,127,005 and horizontal bearings are shown in U.S. Pat. No. 4,130,995.

Figure 2:
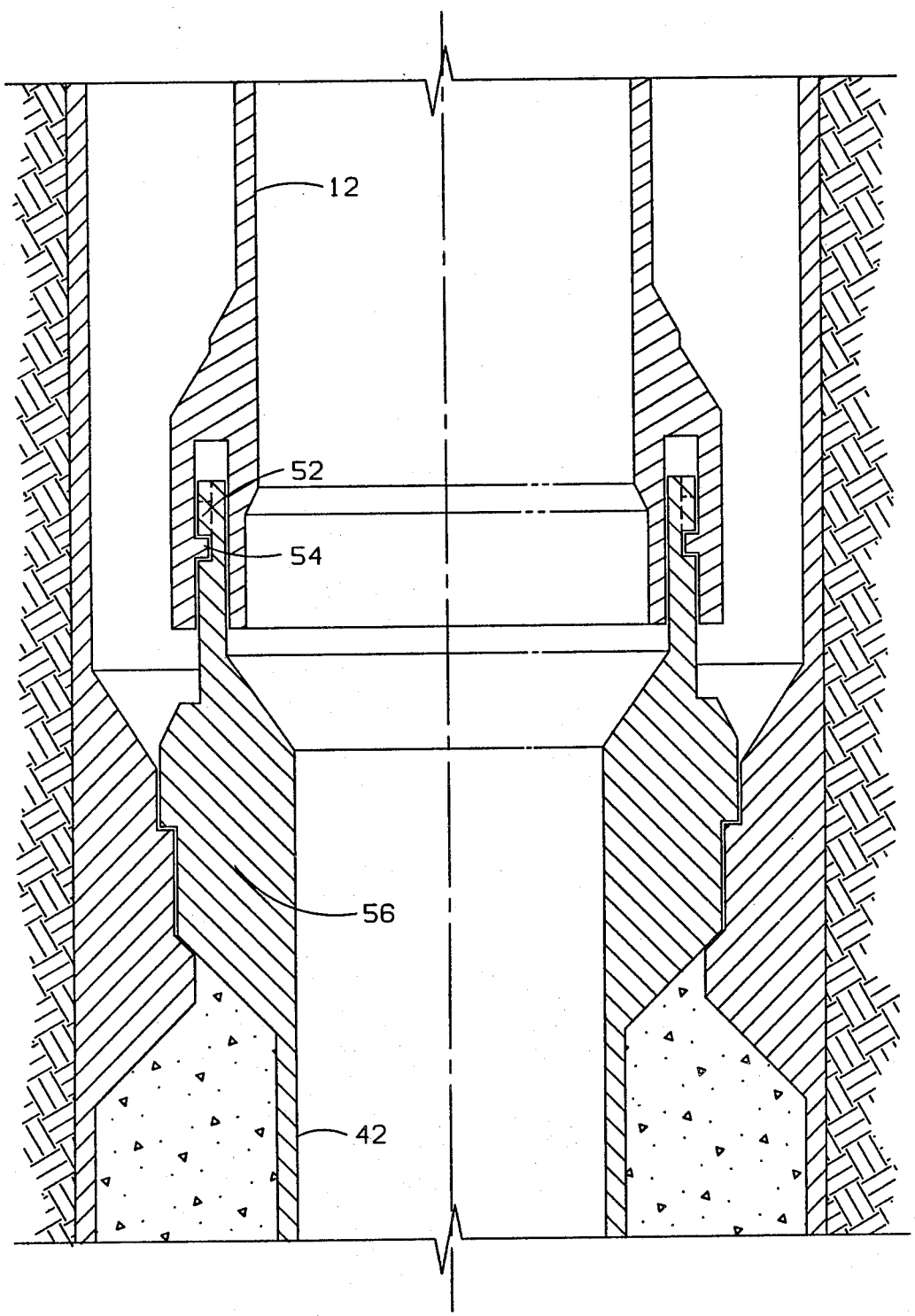
FIG. 2 illustrates a "J" connector between the upper end of a set casing and the lower end of the riser pipe.

Attention is next directed to FIG. 2 which shows an enlarged view of the connector. Shown thereon is a "J" slot connector having a slot 52 on the upper exterior end of conductor casing 42 and a "J" lug 54 on the lower interior of riser pipe 12. It is to be noted, however, that the connector between riser pipe 12 and conductor 42 can be of many and varied types. It is also shown that conductor casing 42 is latched into a mud-line suspension system 56. Such suspension systems are well known and will not be described herein. Most of the various components of a Vertically Moored Platform can be retrieved and fully nondestructively tested on the deck of the VMP or onshore or inspected in-place. One notable exception is the inspection of the connector secured to the upper part of conductor 42 such as "J" slot 52. The riser pipe 12 can be released from the connector and raised to the surface and its connector 54 can be visibly inspected. However, it is impossible to pull the conductor casing 42 inasmuch as it has been set in cement to perform as an anchor. The present invention discloses a new radiographic inspection tool which can be utilized for examining this connection for any cracks due to fatigue or overstressing. This radiographic inspection tool is diagrammatically shown on FIG. 3. This involves a film cowl 62 which can be a cylindrical housing having a means for carrying a radioactive sensitive film 64 on the interior thereof. Alignment bracket 66 is provided at the lower end of cowl 62. The upper end of cowl 62 is provided with a plate 68 or frame to which is connected a drill pipe 70 which is used for lowering and raising the inspection tool. The tool will be lowered through water, therefore, it might be desirable to protect the film 64 with a thin cylindrical sheet 72 of plastic or some other similar material. A point radiographic source 74 is suspended within the cowl 62 and is supported by control cable 76 which permits source 74 to be activated from the surface. Point sources of radiographic tools are well known.

When it is desired to inspect the connector 52, the riser pipe 12, as shown in FIG. 2, is disconnected therefrom and raised to the surface in a known manner. Thereafter the inspection tool is connected to drill pipe 70 and is lowered until the alignment bracket 66 directs the cowl 62 over the upper end of the conductor 42 to be in the position shown in FIG. 3.

Figure 3:
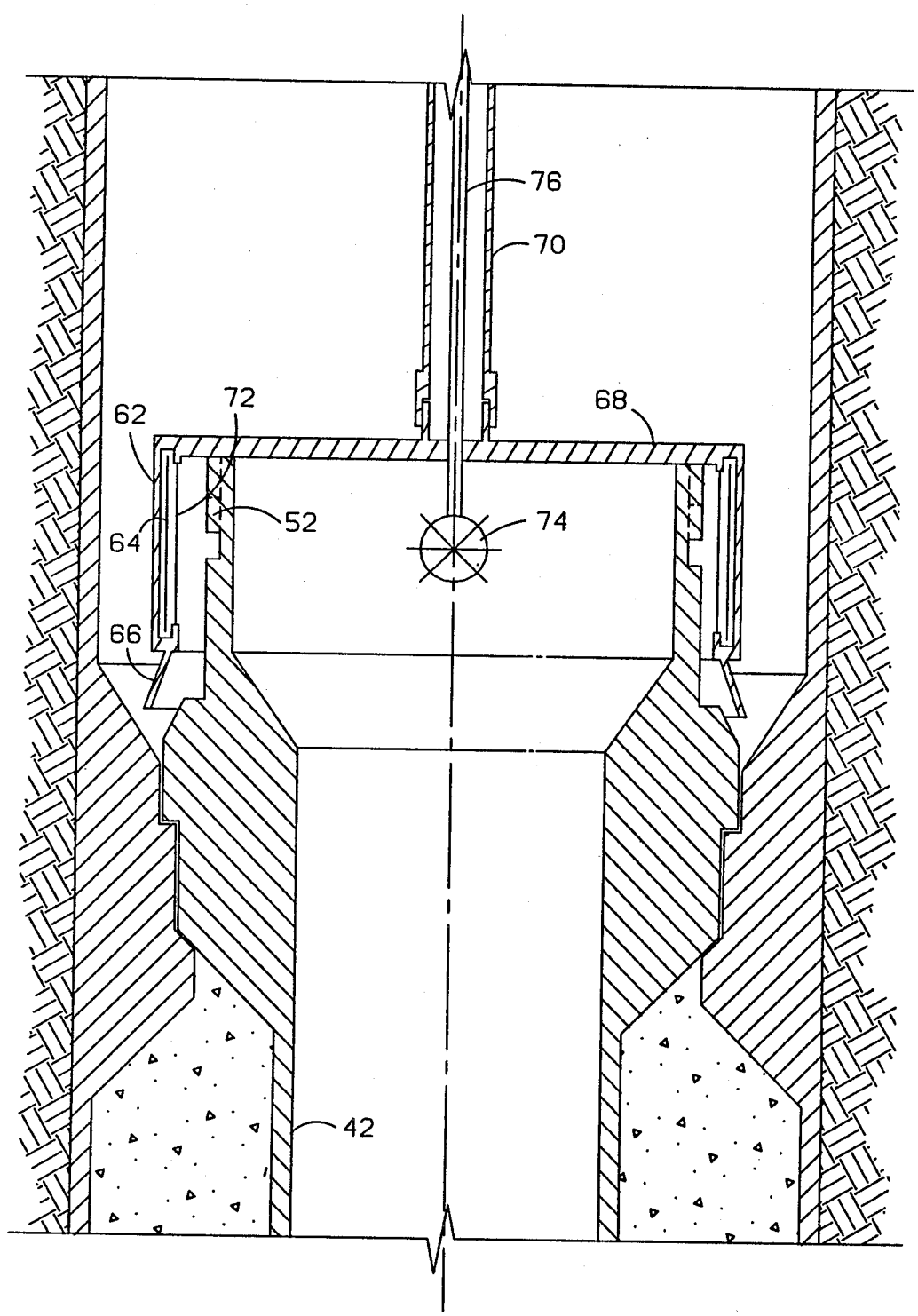
FIG. 3 illustrates the inspection tool in a position to inspect the upper end of the set casing string.

When it is determined that the inspection tool is in the position shown, radiographic source 74 is energized and an image is then imposed upon radiographic film 64, which when developed, will indicate whether there are any cracks in the connector due to fatigue or overstressing or other reasons. One method of insuring that the inspection tool is in the proper location would be by lowering it until plate 68 rests on the top of the "J" slot 52 as shown in FIG. 3.

The inspection tool is now ready to be raised to the surface. This is done by raising drill pipe 70 in the normal manner and also reeling in control cable 76. When the inspection tool reaches the surface, the film 64 is then processed and inspected to determine if there are any cracks in the connector 52.

While the above invention has been described in detail, it is possible to make various modifications therein without departing from the spirit or scope of the invention.

What is claimed:

1. A method of inspecting the connector on the upper end of a string of casing set in the floor of a body of water which comprises:
   attaching an inspection tool to the lower end of a string of drill pipe, said inspection tool having a cylindrical housing, a radiographic film carried by said housing, and a radiographic source,
   lowering said inspection tool so that said cylindrical housing surrounds said connector,
   activating said radiographic source, and
   retrieving said inspection tool.

2. An inspection tool for use with an open-ended casing having a part of a connector on the wall of said casing which comprises:
   a cylindrical housing having one end open and larger than said casing,
   a radiographic source carried within said housing,
   a radiographic film carried on the interior of said housing,
   means to energize said radiographic source from a location remote from said inspection tool, and
   means to connect said housing to a drill pipe.

3. An inspection tool for use with an open-ended casing having a part of a connector on the wall of said casing which comprises:
   a cylindrical housing having one end open and larger than said casing,
   a radiographic source carried within said housing,
   radiographic film carried on the interior of and supported by said housing,
   means to energize said radiographic source from a location remote from said inspection tool, and
   alignment means at one end of said housing.

* * * * *